United States Patent [19]
Satoh et al.

[11] Patent Number: 5,276,058
[45] Date of Patent: Jan. 4, 1994

[54] 3,4-DIHYDROXYCHALCONE DERIVATIVES

[75] Inventors: Toshio Satoh; Hitoshi Matsumoto; Yasunori Niiro, all of Tokushima, Japan

[73] Assignee: Nippon Hypox Laboratories Incorporated, Tokyo, Japan

[21] Appl. No.: 73,423

[22] Filed: Jun. 9, 1993

[51] Int. Cl.$^5$ ............................................. A61K 31/135
[52] U.S. Cl. ................... 514/646; 514/685; 568/334; 564/443
[58] Field of Search ............... 514/643, 685; 568/334; 564/443

[56] References Cited

U.S. PATENT DOCUMENTS

| | | | |
|---|---|---|---|
| 3,137,621 | 6/1964 | Lafon | 514/685 |
| 4,219,569 | 8/1980 | Glenn | 514/685 |
| 4,279,930 | 7/1981 | Hall et al. | 514/646 |
| 4,605,674 | 8/1986 | Fujiu et al. | 514/685 |

FOREIGN PATENT DOCUMENTS

| | | | |
|---|---|---|---|
| 1124254 | 5/1982 | Canada | 568/334 |
| 61-76433 | 4/1986 | Japan | 568/334 |
| 05137 | 4/1992 | World Int. Prop. O. | 568/334 |

*Primary Examiner*—James H. Reamer
*Attorney, Agent, or Firm*—Nixon & Vanderhye

[57] ABSTRACT

Novel 3,4-dihydroxychalcone derivatives useful as a pharmaceutical material, and novel anti-inflammatory preparations. The 3,4-dihydroxychalcone derivatives are compounds of the formula [I],

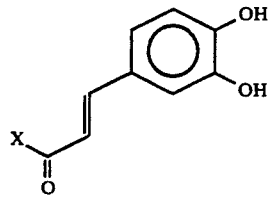

wherein X is a substituted phenyl group represented, e.g., by the formula (i),

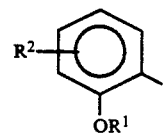

in which $R^1$ is a hydrogen atom or an alkyl group and $R^2$ is an alkyl group, an alkoxy group or an —OH group (excluding an OH-group in the 4-position) or salts thereof. The anti-inflammatory preparations contain one of the above 3,4-dihydroxychalcone derivatives as an active ingredient.

11 Claims, No Drawings

3,4-DIHYDROXYCHALCONE DERIVATIVES

BACKGROUND OF THE INVENTION

1. Field of the Invention

The present invention relates to chalcone derivatives and a pharmaceutical preparation containing one of the chalcone derivatives. In particular, it relates to 3,4-dihydroxychalcone derivatives and an anti-inflammatory preparation containing one of the 3,4-dihydroxychalcone derivatives.

2. Prior Art

It is known that 3,4-dihydroxychalcone and its derivatives have the activity to inhibit the oxidation of edible oils [Food Chemistry (1983, 12) 205-212].

JP,A 61-76433 discloses that 3-(3,4-dihydroxyphenyl)-1-(2,3,4-trimethoxyphenyl)-2-propen-1-one [=3,4-(2',3',4'-trimethoxy)dihydroxychalcone] has anti-allergic activity, and JP,A 63-297847 discloses that 2',3',3,4-tetrahydroxychalcone has extensive anti-inflammatory activity.

Further, although based on in vitro experimental results, it has been revealed that 3,4-dihydroxychalcone and 3,4-dihydroxychalcone derivatives such as 2',3,4-trihydroxychalcone, 4',3,4-trihydroxychalcone and 2',4',3,4-tetrahydroxychalcone have the inhibiting activity have the inhibiting activity against enzymes which are to cause inflammation [PROSTAGLADINSS (1985, 30 (3) 357)].

As described above, studies are now under way concerning the activities of a variety of 3,4-dihydroxychalcone derivatives.

SUMMARY OF THE INVENTION

It is a first object of the present invention to provide novel 3,4-dihydroxychalcone derivatives useful as pharmaceutical materials.

It is a second object of the present invention to provide a novel anti-inflammatory preparation.

According to the present invention, the above first object of the present invention is achieved by novel 3,4-dihydroxychalcone derivatives which are compounds of the formula (I).

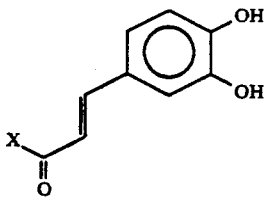

wherein X is a substituted phenyl group represented by the formula (i),

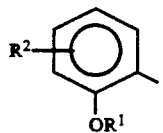

in which $R^1$ is a hydrogen atom or an alkyl group and $R^2$ is an alkyl group, an alkoxy group or an —OH group (excluding an OH-group in the 4-position), the formula (ii),

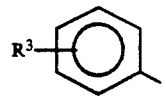

in which $R^3$ is an alkyl group, an alkoxy group or a dimethylamino group, the formula (iii),

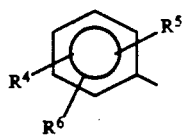

in which each of $R^4$ and $R^5$ is an alkyl group and $R^6$ is a hydrogen atom or an alkyl group, or the formula (iv).

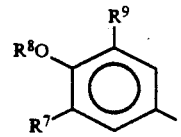

in which $R^7$ is an alkoxy group, $R^8$ is a hydrogen atom or an alkyl group and $R^9$ is a hydrogen atom or an alkoxy group, or salts thereof.

Further, according to the present invention, the above second object of the present invention is achieved by an anti-inflammatory preparation containing one of the above 3,4-dihydroxychalcone derivatives as an active ingredient.

DETAILED DESCRIPTION OF THE INVENTION

The present inventors have made diligent studies of 3,4-dihydroxychalcone derivatives and found that some of the 3,4-dihydroxychalcone derivatives have at least one of the anti-inflammatory activity (particularly when applied topically or externally), inhibiting activity against the oxidation of mammalian cytoplasmic membrane, cyclooxygenase inhibiting activity and lipoxygenase inhibiting activity. On the basis of this finding, the present invention has been completed.

First, the 3,4-dihydroxychalcone derivatives of the present invention are explained hereinafter.

The 3,4-dihydroxychalcone derivatives are compounds of the above formula (I) or salts thereof. When the 3,4-dihydroxychalcone derivatives are compounds of the formula (I) in which X is a substituted phenyl group represented by the formula (i),

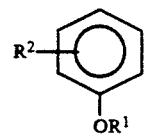

in which $R^1$ is a hydrogen atom or an alkyl group and $R^2$ is an alkyl group, an alkoxy group or an —OH group (excluding an OH-group in the 4-position), specific examples of the alkyl groups as $R^1$ and $R^2$ include methyl, ethyl, n-propyl, isopropyl, n-butyl, isobutyl and tert-butyl. The alkyl group as $R^1$ and the alkyl group as $R^2$ may be the same or different. Specific examples of the alkoxy group as $R^2$ include methoxy, ethoxy, n-propoxy, isopropoxy, n-butoxy, isobutoxy and tert-butyoxy.

When the 3,4-dihydroxychalcone derivatives are compounds of the formula (I) in which X is a substituted phenyl group represented by the formula (ii),

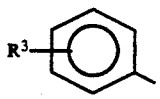

in which $R^3$ is an alkyl group, an alkoxy group or a dimethylamino group.

the formula (iii)

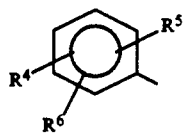

in which each of $R^4$ and $R^5$ is an alkyl group and $R^6$ is a hydrogen atom or an alkyl group, or the formula (iv),

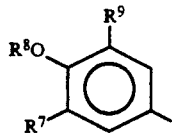

in which $R^7$ is an alkoxy group, $R^8$ is a hydrogen atom or an alkyl group and $R^9$ is a hydrogen atom or an alkoxy group, specific examples of the alkyl group as $R^3$, $R^4$, $R^5$, $R^6$ or $R^8$ include those described regarding the case where the 3,4-dihydroxychalcone derivatives are compounds of the formula (I) in which X is represented by the formula (i). Similarly, specific examples of the alkoxy group as $R^3$, $R^7$ or $R^9$ include those described regarding the case where the 3,4-dihydroxychalcone derivatives are compounds of the formula (I) wherein X is represented by the formula (i).

The novel compounds of the above formula (I) can be produced, for example, by subjecting 3,4-hydroxybenzaldehyde and a substituted acetophenone containing predetermined substituent(s) on its phenyl group to a condensation reaction in an alcoholic reaction solvent under either alkaline or acidic conditions.

All the chalcone compounds of the above formula (I) which can be produced by the above method, or the like have at least one of the anti-inflammatory activity (particularly when applied topically or externally), inhibiting activity against the oxidation of mammalian cytoplasmic membrane, cyclooxygenase inhibiting activity and lipoxygenase inhibiting activity. Therefore, these chalcone compounds are useful as a material for an anti-inflammatory preparation, particularly for a topical or external anti-inflammatory preparation. Further, the above chalcone compounds are also useful as a material for a drug such as a cell protection preparation, a cyclooxygenase inhibiting preparation or a lipoxygenase inhibiting preparation.

Further, like the chalcone compounds of the formula (I), the salts of the compounds of the above formula (I) (e.g., sodium salts and potassium salts) have at least one of the anti-inflammatory activity (particularly when applied topically or externally), inhibiting activity against the oxidation of mammalian cytoplasmic membrane, cyclooxygenase inhibiting activity and lipoxygenase inhibiting activity. Therefore, these salts are also useful not only as a material for an anti-inflammatory preparation, particularly for a topical or external anti-inflammatory preparation, but also as a material for a drug such as a cell protection preparation, a cyclooxygenase inhibiting preparation or a lipoxygenase inhibiting preparation. These salts can be prepared in the usual way.

The anti-inflammatory preparation of the present invention will be explained hereinafter. As described already, the anti-inflammatory preparation contains one of the compounds of the above formula (I) or the salts thereof as an active ingredient.

The anti-inflammatory preparation of the present invention is particularly efficacious when applied topically or externally. When the anti-inflammatory preparation is used as a topical application drug or external medicine, specific examples of the preparation form include the forms of an ointment, a liquid preparation (including clear solution, emulsion and suspension, the liquid preparation being used in this sense hereinafter), a suppository, an ophthalmic solution and a sticking preparation although it shall not be limited to these forms.

Further, the anti-inflammatory preparation of the present invention may be used as a preparation for systemic or internal application. Specific examples of this preparation include the forms of a tablet, a capsule, granules, a dispersion, a powder, a pill, a troche, a syrup and a solution, although it shall not be limited to these forms. Further, the anti-inflammatory preparation of the present invention may also be used as an injection.

The anti-inflammatory preparation of the present invention can be prepared, by any one of known methods, from a 3,4-dihydroxychalcone derivative which is one of the compounds of the formula (I) or the salts thereof and toxicity-free additives generally used for forming preparations and selected from a vehicle, a binder, a lubricant, a disintegrant, an antiseptic, a tonicity agent, a stabilizer, a disperser, an antioxidant, a colorant, a flavor and a buffer. The additives used for forming the preparation differ depending upon the form of the intended pharmaceutical preparation. Specific examples of the toxicity-free additives include starch, gelatin, glucose, lactose, fructose, maltose, magnesium carbonate, magnesium stearate, methyl cellulose, carboxymethyl cellulose, gum arabic, polyethylene glycol, propylene glycol, Vaseline, Carbowax, glycerin, ethanol, syrup, sodium chloride, sodium sulfite, sodium phosphate, citric acid, polyvinyl pyrrolidone and water.

The content of the 3,4-dihydroxychalcone derivative of the present invention in the anti-inflammatory preparation of the present invention differs depending upon the preparation form and use, while this content is generally preferably 0.01 to 99% by weight.

The dose of the 3,4-dihydroxychalcone derivative may be widely varied depending upon the kind of animals, age, sex, the kind of disease, symptoms, diagnosis results, while the dose can be 0.01 to 100 mg/kg per day. The dose can be also varied according to conditions of symptoms of a patient and medical practitioner's diagnosis results. The above dose may be administered once a day or in some separate portions a day.

The pharmaceutical preparation of the present invention may further contain other therapeutically useful medicament as an active ingredient in addition to the 3,4-dihydroxychalcone derivative of the present invention.

EXAMPLES

The present invention will be further explained hereinafter by reference to Examples.

EXAMPLE 1

Preparation of 2',5'-dimethoxy-3,4-dihydroxychalcone 2.7 Grams (19.6 mmol) of 3,4-dihydroxybenzaldehyde and 0.12 g (0.5 mmol) of pyridine p-toluenesulfonate were suspended in 40 ml of methylene chloride, and a solution of 10.1 g (120 mmol) of 3,4-dihydro-2H-pyran in 10 ml of methylene chloride was gradually added dropwise with stirring. After 2.5 hours, 0.4 g of 3,4-dihydro-2H-pyran was added, and the mixture was further stirred for 1 hour. Then, the reaction mixture was consecutively washed with 0.5N HCl, with 5% NaHCO$_3$ and with water, and an organic layer was distilled off under reduced pressure to give 5.9 g of a reaction product.

3.1 Grams of the above reaction product, 1.8 g (10.0 mmol) of 2',5'-dimethoxyacetophenone and 3.2 g (10.2 mmol) of Ba(OH)$_2$.8H$_2$O were dissolved in 100 ml of methanol, and the mixture was stirred overnight. After the reaction, the reaction mixture was adjusted to pH 6, methanol was distilled off, and the residue was subjected to extraction with ethyl acetate. The extracted product was washed with water and an organic layer was distilled off to give 6.7 g of a reaction product.

6.7 Grams of the above reaction product was dissolved in 100 ml of methanol, 200 mg (1.1 mmol) of p-toluenesulfonic acid was added, and the mixture was stirred overnight. Then, the methanol was distilled off, and the residue was recrystallized from benzene-acetone to give 0.6 g of the captioned compound (yield 20%).

Table 1 shows the melting point, ultraviolet light absorption characteristics, HPLC analysis values and NMR analysis values of the so-obtained captioned compound.

EXAMPLES 2-30

3,4-Dihydroxychalcone derivatives shown in Tables 1 to 8 were obtained in the same manner as in Example 1 except that the substituted acetophenone was changed as shown in Tables 1 to 8.

Table 1 to 8 show the melting points, ultraviolet light absorption characteristics, HPLC analysis values and NMR analysis values of the so-obtained 3,4-dihydroxychalcone derivatives.

TABLE 1

| Ex. No. | X | mp | UV absorption | HPLC analysis | NMR analysis (CDCl$_3$ + DMSO-d$_6$; δ) |
|---|---|---|---|---|---|
| 1 | OCH$_3$ / [formula(i)] / OCH$_3$ | 158~160(°C.) | λmax 359.2 nm ε=1.58×10$^4$ | R. t.=4.28 K'=1.45 | 8.08(s, 1H, aromatic-OH), 7.74(s, 1H, aromatic-OH), 7.51(d, 1H, J=16Hz, olefinic), 7.18(d, 1H, J=16Hz, olefinic), 7.16(d, 1H, J=2Hz, Ar), 7.13(d, 1H, J=3Hz, Ar), 7.04~6.91(m, 3H, Ar), 6.87 (d, 1H, J=8Hz, Ar), 3.84(s, 3H, 2'-aromatic-OCH$_3$), 3.80(s, 3H, 5'- aromatic-OCH$_3$) |
| 2 | CH$_3$O / [formula(i)] / OCH$_3$ | 160~161(°C.) | λmax 361.0 nm ε=2.31×10$^4$ | R. t.=4.47 K'=1.54 | 8.02(bs, 1H, aromatic-OH), 7.70(d, 1H, J=9Hz, Ar), 7.67(d, 1H, J=9Hz, Ar), 7.56(d, 1H, J=16Hz, olefinic), 7.30(d, 1H, J=16Hz, olefinic), 7.17(d, 1H, J=2Hz, Ar), 7.04~6.99(m, 1H, Ar), 6.87(d, 1H, J=8Hz, Ar), 6.58~6.53(m, 1H, Ar), 6.50(d, 1H, J=2Hz, Ar), 3.90(s, 3H, 2'-aromatic-OCH$_3$), 3.87(s, 3H, 4'-aromatic-OCH$_3$) |
| 3 | OH / [formula(i)] / OH | 204~205(°C.) | λmax 385.1 nm ε=1.74×10$^4$ | R. t.=4.12 K'=1.34 | 12.40(s, 1H, 2'-aromatic-OH), 8.53(s, 1H, aromatic-OH), 8.48 (s, 1H, 5'-aromatic-OH), 8.11(s, 1H, aromatic-OH), 7.79(d, 1H, J=15Hz, olefinic), 7.43(d, 1H, J=15Hz, olefinic), 7.41(d, 1H, J=3Hz, Ar), 7.25(d, 1H, J=2Hz, Ar), 7.10~7.05(m, 2H, Ar ), 6.90 (d, 1H, J=8Hz, Ar), 6.85(d, 1H, J=9Hz, Ar) |
| 4 | CH$_3$O / [formula(i)] / OH | 170~173(°C.) | λmax 383.9 nm ε=1.04×10$^4$ | R. t.=7.74 K'=3.42 | 13.60(s, 1H, 2'-aromatic-OH), 8.27(bs, 1H, aromatic-OH), 7.83 (d, 1H, J=9Hz, Ar), 7.79(d, 1H, J=15Hz, olefinic), 7.23(d, 1H, J=2Hz, Ar), 7.11~7.06(m, 1H, Ar), 6.90(d, 1H, J=8Hz, Ar), 6.51~6.46(m, 1H, Ar), 6.48(d, 1H, J=8Hz, Ar), 3.86(s, 3H, 4'-aromatic-OCH$_3$) |

TABLE 2

| Ex. No. | X | mp | UV absorption | HPLC analysis | NMR analysis (CDCl$_3$+ DMSO-d$_6$; δ) |
|---|---|---|---|---|---|
| 5 | CH$_3$-C$_6$H$_3$(OH)- [formula(i)] (4-OH, 3-CH$_3$ phenyl) | 177~182.5 (°C.) | λmax 386.0 nm ε=2.3×10$^4$ | R. t.=10.79 K'=4.62 | 12.79(s, 1H, 2'-aromatic-OH), 8.20(bs, 1H, aromatic-OH), 7.82 (d, 1H, J=15Hz, olefinic), 7.69(d, 1H, J=2Hz, Ar), 7.66(bs, 1H, aromatic-OH), 7.48(d, 1H, J=15Hz, olefinic), 7.33~7.27(m, 1H, Ar), 7.26(d, 1H, J=2Hz, Ar), 7.14~7.09(m, 1H, Ar), 6.92(d, 2H, J=8Hz, Ar), 2.35(s, 3H, 5'-aromatic-CH$_3$) |
| 6 | OCH$_3$-C$_6$H$_3$(OH)- [formula(i)] | 149~151 (°C.) | λmax 387 nm ε=3.78×10$^4$ | R. t.=7.91 K'=3.12 | 12.56(s, 1H, 2'-aromatic-OH), 8.22(bs, 1H, aromatic-OH), 7.84 (d, 1H, J=15Hz, olefinic), 7.65(bs, 1H, aromatic-OH), 7.42(d, 1H, J=15Hz, olefinic), 7.36(d, 1H, J=3Hz, Ar), 7.25(d, 1H, J=2Hz, Ar), 7.16~7.09(m, 2H, Ar ), 6.96(d, 1H, J=9Hz, Ar), 6.92 (d, 1H, J=8Hz, Ar), 3.85(s, 3H, 5'-aromatic-OCH$_3$) |
| 7 | (CH$_3$)$_2$CH-C$_6$H$_3$(OH)- [formula(i)] | 157~158 (°C.) | λmax 386.8 nm ε=1.15×10$^4$ | R. t.=25.27 K'=21.71 | 12.83(s, 1H, 2'-aromatic-OH), 8.20(bs, 1H, aromatic-OH), 7.83 (d, 1H, J=15Hz, olefinic), 7.71(d, 1H, J=2Hz, Ar), 7.67(bs, 1H, aromatic-OH), 7.49(d, 1H, J=15Hz, olefinic), 7.40~7.35(m, 1H, Ar), 7.27(d, 1H, J=2Hz, Ar), 7.14~7.10(m, 1H, Ar), 6.94(d, 1H, J=8Hz, Ar), 6.92(d, 1H, J=8Hz, Ar), 3.01~2.81(m, 1H, 5'-aromatic-CH, 1.29(d, 6H, J=1Hz, —CH(C$\underline{H}_3$)$_2$) |
| 8 | (CH$_3$)$_2$CH-O-C$_6$H$_3$(OH)- [formula(i)] | 176.5~178 (°C.) | λmax 388.6 nm ε=1.76×10$^4$ | R. t.=15.13 K'=7.65 | 12.53(s, 1H, 2'-aromatic-OH), 8.18(s, 1H, aromatic-OH), 7.83 (d, 1H, J=15Hz, olefinic), 7.66(s, 1H, aromatic-OH), 7.41(d, 1H, J=15Hz, olefinic), 7.40(d, 1H, J=3Hz, Ar), 7.25(d, 1H, J=2Hz, Ar), 7.15~7.08(m, 2H, Ar), 6.94(d, 1H, J=9Hz, Ar), 6.92(d, 1H, J=8Hz, Ar), 4.50~4.44(m, 1H, 5'-aromatic-O—CH, 1.36(s, 3H, —O(C$\underline{H}_3$)$_2$), 1.33(s, 3H, —O(C$\underline{H}_3$)$_2$) |

TABLE 3

| Ex. No. | X | mp | UV absorption | HPLC analysis | NMR analysis (CDCl$_3$+ DMSO-d$_6$; δ) |
|---|---|---|---|---|---|
| 9 | OC$_4$H$_9$-C$_6$H$_3$(OH)- [formula(i)] | 162~163 (°C.) | λmax 388 nm ε=3.08×10$^4$ | R. t.=33.84 K'=19.14 | 12.53(s, 1H, 2'-aromatic-OH), 8.42(bs, 1H, aromatic-OH), 8.11 (d, 1H, J=15Hz, olefinic), 7.83(bs, 1H, aromatic-OH), 7.42(d, 1H, J=16Hz, olefinic), 7.37(d, 1H, J=3Hz, Ar), 7.26(d, 1H, J=2Hz, Ar), 7.15~7.08(m, 2H, Ar), 6.94(d, 1H, J=9Hz, Ar), 6.92 (d, 1H, J=8Hz, Ar), 3.98(t, 2H, J=6Hz, —O—CH$_2$—C), 1.83~1.74(m, 2H, C—CH$_2$—C), 1.62~1.42(m, 2H, C—CH$_2$—C), 1.00(t, 3H, J=7Hz, C—CH$_3$) |
| 10 | OC$_2$H$_5$-C$_6$H$_3$(OH)- [formula(i)] | 167~169 (°C.) | λmax 388.0 nm ε=2.48×10$^4$ | R. t.=19.0 K'=7.09 | 12.54(s, 1H, 2'-aromatic-OH), 8.43(bs, 1H, aromatic-OH), 7.85 (bs, 1H, aromatic-OH), 7.83(d, 1H, J=15Hz, olefinic), 7.42(d, 1H, J=15Hz, olefinic), 7.38(d, 1H, J=3Hz, Ar), 7.25(d, 1H, J=2Hz, Ar), 7.15~7.09(m, 2H, Ar), 6.94(d, 1H, J=9Hz, Ar), 6.91 (d, 1H, J=8Hz, Ar), 4.05(q, 2H, J=7Hz, —O—CH$_2$—C), 1.44(t, 3H, J=7Hz, C—CH$_3$) |
| 11 | CH$_3$-C$_6$H$_3$(OCH$_3$)- [formula(i)] | 149.5~151 (°C.) | λmax 360.8 nm ε=2.25×10$^4$ | R. t.=5.94 K'=2.39 | 8.04(s, 1H, aromatic-OH), 7.72(s, 1H, aromatic-OH), 7.49(d, 1H, J=16Hz, olefinic), 7.36(d, 1H, J=2Hz, Ar), 7.27~7.22(m, 1H, Ar), 7.15(d, 1H, J=16Hz, olefinic), 7.15(d, 1H, J=2Hz, Ar), 7.02~6.97(m, 1H, Ar), 6.89(m, 1H, J=8Hz, Ar), 6.86(d, 1H, J=8Hz, Ar), 3.81(s, 3H, 2'-aromatic-OCH$_3$), 2.32(s, 3H, 5'-aromatic-CH$_3$) |
| 12 | (OCH$_3$)$_2$-C$_6$H$_3$- [formula(i)] | 192~194 (°C.) | λmax 350 nm ε=2.47×10$^4$ | R. t.=3.15 K'=0.96 | 7.83(bs, 1H, aromatic-OH), 7.76(bs, 1H, aromatic-OH), 7.31 (t, 1H, J=8Hz, Ar), 7.18(d, 1H, J=16Hz, olefinic), 7.09(d, 1H, J=2Hz, Ar), 6.94~6.89(m, 1H, Ar), 6.83(d, 1H, J=8Hz, Ar), 6.76 (d, 1H, J=16Hz, olefinic), 6.60(d, 2H, J=8Hz, Ar), 3.77(s, 6H, 2',6'-aromatic-OCH$_3$) |

TABLE 4

| Ex. No. | X | mp | UV absorption | HPLC analysis | NMR analysis (CDCl$_3$+ DMSO-d$_6$; δ) |
|---|---|---|---|---|---|
| 13 | OC$_2$H$_5$ / OCH$_3$ (benzene ring with OC$_2$H$_5$, CH$_3$, OCH$_3$) [formula(i)] | 115~122 (°C.) | λmax 359.3 nm ε=3.37×10$^4$ | R. t.=8.43 K'=2.602 | 7.99(bs, 1H, aromatic-OH), 7.68(bs, 1H, aromatic-OH), 7.51 (d, 1H, J=16Hz, olefinic), 7.18(d, 1H, J=16Hz, olefinic), 7.16 (d, 1H, J=2Hz, Ar), 7.12(d, 1H, J=3Hz, Ar), 7.03~6.98(m, 2H, Ar), 6.91(d, 1H, J=10Hz, Ar), 6.87(d, 1H, J=8Hz, Ar), 4.02(q, 2H, J=7Hz, —O—CH$_2$—C), 3.84(s, 3H, —OCH$_3$), 1.40(t, 3H, J=7Hz, O—C—CH$_3$) |
| 14 | CH$_3$\_CH$_3$ / OCH$_3$ (isopropoxy, CH$_3$, OCH$_3$ on benzene) [formula(i)] | 42 (°C.) | λmax 359.5 nm ε=2.36×10$^4$ | R. t.=11.08 K'=3.71 | 7.56(d, 1H, J=16Hz, olefinic), 7.21(d, 1H, J=16Hz, olefinic), 7.20(d, 1H, J=2Hz, Ar), 7.15(d, 1H, J=3Hz, Ar), 7.08~6.99(m, 2H, Ar), 6.91(d, 1H, J=9Hz, Ar), 6.88(d, 1H, J=8Hz, Ar), 4.53~4.40(m, 1H, 5'-O—CH), 3.83(s, 3H, 2'-OCH$_3$), 1.33(s, 3H, 5'-O(CH$_3$)$_2$), 1.30(s, 3H, 5'-O(CH$_3$)$_2$) |
| 15 | OCH$_3$ / OC$_2$H$_5$ [formula(i)] | 122~125 (°C.) | λmax 361.9 nm ε=3.60×10$^4$ | R. t.=8.46 K'=2.60 | 8.14(bs, 1H, aromatic-OH), 7.80(bs, 1H, aromatic-OH), 7.53 (d, 1H, J=16Hz, olefinic), 7.30(d, 1H, J=16Hz, olefinic), 7.17 (d, 1H, J=3Hz, Ar), 7.16(d, 1H, J=2Hz, Ar), 7.04~6.97(m, 2H, Ar), 6.91(d, 1H, J=8Hz, Ar), 4.06(q, 2H, J=7Hz, O—CH$_2$—C), 3.80(s, 3H, —OCH$_3$), 1.39(t, 3H, J=7Hz, —OC—CH$_3$) |
| 16 | OC$_2$H$_5$ / OC$_2$H$_5$ [formula(i)] | 153~155 (°C.) | λmax 358.7 nm ε=1.03×10$^4$ | R. t.=12.13 K'=4.16 | 7.94(bs, 1H, aromatic-OH), 7.64(bs, 1H, aromatic-OH), 7.53 (d, 1H, J=16Hz, olefinic), 7.29(d, 1H, J=16Hz, olefinic), 7.16 (d, 1H, J=2Hz, Ar), 7.16(d, 1H, J=2Hz, Ar), 7.00~6.96(m, 2H, Ar), 6.90(d, 1H, J=9Hz, Ar), 6.87(d, 1H, J=8Hz, Ar), 4.11~3.97(m, 4H, —O—CH$_2$—C), 1.43~1.35(m, 6H, —O—C—CH$_3$) |

TABLE 5

| Ex. No. | X | mp | UV absorption | HPLC analysis | NMR analysis (CDCl$_3$+ DMSO-d$_6$; δ) |
|---|---|---|---|---|---|
| 17 | CH$_3$ (3-methylphenyl) [formula(ii)] | 163.5~164 (°C.) | λmax 364.0 nm ε=2.37×10$^4$ | R. t.=7.61 K'=2.96 | 8.17(bs, 1H, aromatic-OH), 7.80~7.77(m, 3H, Ar and aromatic-OH), 7.70(d, 1H, J=16Hz, olefinic), 7.39~7.36(m, 2H, Ar), 7.34(d, 1H, J=16Hz, olefinic), 7.22(d, 1H, J=2Hz, Ar), 7.10~7.05(m, 1H, Ar), 6.90(d, 1H, J=8Hz, Ar), 2.44(s, 3H, 3'- aromatic -CH$_3$) |
| 18 | CH$_3$ (4-methylphenyl) [formula(ii)] | 201~201.5 (°C.) | λmax 366 nm ε=2.40×10$^4$ | R. t.=7.39 K'=2.85 | 8.14(bs, 1H, aromatic-OH), 7.91(d, 2H, J=8Hz, Ar), 7.78(bs, 1H, aromatic-OH), 7.70(d, 1H, J=16Hz, olefinic), 7.34(d, 1H, J=15Hz, olefinic), 7.29(d, 2H, J=8Hz, Ar), 7.21(d, 1H, J=2Hz, Ar), 7.09~7.04(m, 1H, Ar), 6.89(d, 1H, J=9Hz, Ar), 2.43(s, 3H, 4'- aromatic-CH$_3$) |
| 19 | OCH$_3$ (2-methoxyphenyl) [formula(ii)] | 146~148 (°C.) | λmax 357 nm ε=2.28×10$^4$ | R. t.=4.24 K'=1.21 | 7.93(s, 1H, aromatic-OH), 7.63(s, 1H, aromatic-OH), 7.58~7.53 (m, 1H, Ar), 7.49(d, 1H, J=16Hz, olefinic), 7.50~7.41(m, 1H, Ar), 7.15(d, 1H, J=2Hz, Ar), 7.15(d, 1H, J=16Hz, olefinic), 7.06~6.97(m, 3H, Ar), 6.86(d, 1H, J=8Hz, Ar), 3.88(s, 3H, 2'-aromatic-OCH$_3$) |
| 20 | CH$_3$O (3-methoxyphenyl) [formula(ii)] | 151.5~152.5 (°C.) | λmax 368.7 nm ε=2.84×10$^4$ | R. t.=5.52 K'=2.14 | 8.03(s, 1H, aromatic-OH), 7.71(d, 1H, J=16Hz, olefinic), 7.67 (s, 1H, aromatic-OH), 7.60~7.51(m, 2H, Ar), 7.40(t, 1H, J=8Hz, Ar), 7.32(d, 1H, J=16Hz, olefinic), 7.22(d, 1H, J=2Hz, Ar), 7.14~7.05(m, 2H, Ar), 6.90(d, 1H, J=8Hz, Ar), 3.88(s, 3H, 3'-aromatic-OCH$_3$) |

TABLE 6

| Ex. No. | X | mp | UV absorption | HPLC analysis | NMR analysis (CDCl$_3$+ DMSO-d$_6$; δ) |
|---|---|---|---|---|---|
| 21 | CH$_3$O—⌬—CH$_3$ [formula(ii)] | 174~176 (°C.) | λmax 364.6 nm ε=2.72 × 10$^4$ | R. t.=5.43 K'=1.83 | 8.20(bs, 1H, aromatic-OH), 8.02(d, 2H, J=9Hz, Ar), 7.83(bs 1H, aromatic-OH), 7.70(d, 1H, J=15Hz, olefinic), 7.36(d, 1H, J=15Hz, Ar), 7.22(d, 1H, J=2Hz, Ar), 7.09~7.05(m, 1H, Ar), 6.98 (d, 2H, J=9Hz, Ar), 6.90(d, 1H, J=8Hz, Ar), 3.89(d, 3H, 4'-aromatic-OCH$_3$) |
| 22 | (CH$_3$)$_2$CH—O—⌬—CH$_3$ [formula(ii)] | 162~164 (°C.) | λmax 364 nm ε=1.87×10$^4$ | R. t.=9.15 K'=4.20 | 8.00(d, 2H, J=9Hz, Ar), 7.97(bs, 1H, aromatic-OH), 7.70(d, 1H, J=16Hz, olefinic), 7.63(bs, 1H, aromatic-OH), 7.36(d, 1H, J=16Hz, olefinic), 7.22(d, 1H, J=2Hz, Ar), 7.10~7.05(m, 1H, Ar), 6.94(d, 2H, J=9Hz, Ar), 6.89(d, 1H, J=8Hz, Ar), 4.67(q, 1H, J=6Hz, 4'-O—CH), 1.39(s, 3H, 4'-O—CH(CH$_3$)$_2$), 1.36(s, 3H, 4'-O—CH(CH$_3$)$_2$) |
| 23 | CH$_3$—N(CH$_3$)—⌬—CH$_3$ (meta) [formula(ii)] | 145~149 (°C.) | λmax 363 nm ε=1.94×10$^4$ | R. t.=5.67 K'=1.91 | 7.69(d, 1H, J=16Hz, olefinic), 7.36~7.32(m, 3H, Ar), 7.32(d, 1H, J=15Hz, olefinic), 7.21(d, 1H, J=2Hz, Ar), 7.07~7.04(m, 1H, Ar), 6.96~6.90(m, 1H, Ar), 6.89(d, 1H, J=8Hz, Ar), 3.02(s, 6H, 3'-aromatic-N(CH$_3$)$_2$) |
| 24 | CH$_3$—N(CH$_3$)—⌬—CH$_3$ (para) [formula(ii)] | 211.2~212.5 (°C.) | λmax 396.1 nm ε=3.49×10$^4$ | R. t.=5.26 K'=1.74 | 7.98(d, 2H, J=9Hz, Ar), 7.68(d, 1H, J=15Hz, olefinic), 7.41(d, 1H, J=15Hz, olefinic), 7.22(d, 1H, J=2Hz, Ar), 7.09~7.04(m, 1H, Ar), 6.89(d, 1H, J=8Hz, Ar), 6.70(d, 2H, J=9Hz, Ar), 3.08(s, 6H, 4'-aromatic-N(CH$_3$)$_2$) |

TABLE 7

| Ex. No. | X | mp | UV absorption | HPLC analysis | NMR analysis (CDCl$_3$+ DMSO-d$_6$; δ) |
|---|---|---|---|---|---|
| 25 | 2,4-(CH$_3$)$_2$-phenyl [formula(iii)] | 130.9~133.5 (°C.) | λmax 355.0 nm ε=3.71×10$^4$ | R. t.=9.48 K'=3.94 | 7.91(s, 1H, aromatic-OH), 7.71(s, 1H, aromatic-OH), 7.41~7.36 (m, 1H, Ar), 7.36(d, 1H, J=16Hz, olefinic), 7.13(d, 1H, J=2Hz, Ar), 7.08~7.04(m, 2H, Ar), 6.99~6.94(m, 1H, Ar), 6.95(d, 1H, J=16Hz, olefinic), 6.86 (d, 1H, J=8Hz, Ar), 2.41 (s, 3H, 2'-aromatic-CH$_3$), 2.37(s, 3H, 4'-aromatic-CH$_3$) |
| 26 | 2,5-(CH$_3$)$_2$-phenyl [formula(iii)] | 154.5~155 (°C.) | λmax 360.0 nm ε=3.19×10$^4$ | R. t.=9.15 K'=4.23 | 7.96(s, 1H, aromatic-OH), 7.75(s, 1H, aromatic-OH), 7.33(d, 1H, J=16Hz, olefinic), 7.23(d, 1H, J=2Hz, Ar), 7.20~7.11(m, 3H, Ar), 7.00~6.95(m, 1H, Ar), 6.91(d, 1H, J=16Hz, olefinic), 6.86(d, 1H, J=8Hz, Ar), 2.36(s, 6H, 2',5'-aromatic-CH$_3$) |
| 27 | 2,4,6-(CH$_3$)$_3$-phenyl [formula(iii)] | 175~176 (°C.) | λmax 352 nm ε=1.89×10$^4$ | R. t.=10.71 K'=4.58 | 7.70(bs, 1H, aromatic-OH), 7.66(bs, 1H, aromatic-OH), 7.08 (d, 1H, J=2Hz, Ar), 7.06(d, 1H, J=16Hz, olefinic), 6.93~6.87 (m, 3H, Ar), 6.84(d, 1H, J=8Hz, Ar), 6.75(d, 1H, J=16Hz, olefinic), 2.32(s, 3H, 4'-aromatic-CH$_3$), 2.17(s, 6H, 2', 6'-aromatic-CH$_3$) |
| 28 | 3-HO, 4-CH$_3$O-phenyl [formula(iii)] | 174~177 (°C.) | λmax 368 nm ε=2.19×10$^4$ | R. t.=2.88 K'=0.48 | 8.24(s, 1H, 3-aromatic-OH), 7.86(s, 2H, 4'4-aromatic-OH), 7.69(d, 1H, J=16Hz, olefinic), 7.63~7.57(m, 1H, Ar), 7.60(d, 1H, J=2Hz, Ar), 7.37(d, 1H, J=15Hz, olefinic), 7.22(d, 1H, J=2Hz, Ar), 7.09~7.04(m, 1H, Ar), 6.97(d, 1H, J=9Hz, Ar), 6.89(d, 1H, J=8Hz, Ar), 3.97(s, 3H, 3'-aromatic-OCH$_3$) |

TABLE 8

| Ex. No. | X | mp | UV absorption | HPLC analysis | NMR analysis (CDCl$_3$+ DMSO-d$_6$; δ) |
|---|---|---|---|---|---|
| 29 | 3,4-(CH$_3$O)$_2$-phenyl [formula(iv)] | 132~137 (°C.) | λmax 367.9 nm ε=2.47×10$^4$ | R. t.=3.50 K'=1.00 | 8.26(bs, 1H, aromatic-OH), 7.82(bs, 1H, aromatic-OH), 7.71 (d, 1H, J=16Hz, olefinic), 7.70~7.65(m, 1H, Ar), 7.61(d, 1H, J=2Hz, Ar), 7.37(d, 1H, J=16Hz, olefinic), 7.22(d, 1H, J=2Hz, Ar), 7.10~7.05(m, 1H, Ar), 6.94(d, 1H, J=8Hz, Ar), 6.90 (d, 1H, J=8Hz, Ar), 3.97(s, 6H, 3',4'-aromatic-OCH$_3$) |

TABLE 8-continued

| Ex. No. | X | mp | UV absorption | HPLC analysis | NMR analysis (CDCl₃+ DMSO-d₆; δ) |
|---|---|---|---|---|---|
| 30 | CH₃O—⟨OCH₃, OCH₃⟩ [formula(iv)] | 153~154 (°C.) | λmax 368.4 nm ε=1.97×10⁴ | R.t.=4.23 K'=1.40 | 8.23(bs, 1H, aromatic-OH), 7.70(d, 1H, J=16Hz, olefinic), 7.69 (bs, 1H, aromatic-OH), 7.29(d, 1H, J=16Hz, olefinic), 7.27(d, 2H, J=9Hz, Ar), 7.22(d, 1H, J=2Hz, Ar), 7.09~7.04(m, 1H, Ar), 6.89(d, 1H, J=8Hz, Ar), 3.93(d, 1H, 3',5'-aromatic-OCH₃), 3.83 (s, 3H, 4'-aromatic-OCH₃) |

TOXICITY TEST

The 3,4-dihydroxychalcone derivatives obtained in Examples 1, 2, 5, 8, 10, 15, 19, 20, 21, 25, 27, 28 and 29 were selected as test compounds and subjected to the following toxicity test.

Each test compound was independently orally administered to male ICR mice weighting about 30 g (3-5 mice/group) in a dose of 1,000 mg/kg. And, after the administration, the mice were observed for an influence of the test compound on general symptoms for 5 hours with time by an Irwin's multibehavior analysis method, and 24 hours after the administration, the mice were also observed in the same manner.

As a control, a 1% gum arabic solution was orally administered in place of the test compound.

As a result, the test compound groups and the control group showed no difference in general symptoms, and the test compounds were found to be free of toxicity.

TOPICAL ANTI-INFLAMMATORY ACTIVITY TEST

The 3,4-dihydroxychalcone derivatives shown in Table 9, as test compounds, were subjected to the following topical anti-inflammatory activity test.

Acetone solutions were prepared from the test compounds. Then, the acetone solution were applied to the right ears of male ICR mice such that the dose of each test compound was 10 μg/ear, 30 μg/ear of 100 μg/ear. One hour after the application, 1 mg of arachidonic acid was applied to each right ear to cause ear swelling.

One hour after the application of the arachidonic acid, the mice were sacrificed by vertebral cervical dislocation, and the right and left ears were taken and separately weighed. The weight of the right ear to which the arachidonic acid had been applied was divided by the weight of the non-treated left ear to obtain a swelling ratio.

The effect of each test compound was shown in the following manner. The relative values of the swelling ratios of individual mice were calculated on an assumption that the average value of the swelling ratios of the solvent control group was taken as 100, and amounts of their decreases were expressed by percentages (inhibition ratios). Table 9 shows the results.

TABLE 9

| | Ratio of inhibition of ear swelling induced by arachidonic acid | | |
|---|---|---|---|
| | 10 μg/ear | 30 μg/ear | 100 μg/ear |
| Compound of Example 1 | — | 77 | — |
| Compound of Example 2 | — | 56 | — |
| Compound of Example 3 | — | 39 | — |
| Compound of Example 4 | — | 35 | — |
| Compound of Example 5 | 31 | 52 | — |
| Compound of Example 6 | 7.6 | 38 | 43 |
| Compound of Example 7 | — | 9.0 | — |
| Compound of Example 8 | — | 67 | — |
| Compound of Example 9 | — | 31 | — |
| Compound of Example 10 | — | 43 | — |
| Compound of Example 11 | — | 32 | — |
| Compound of Example 12 | — | 8.0 | — |
| Compound of Example 13 | — | 13 | — |
| Compound of Example 14 | — | 33 | — |
| Compound of Example 15 | — | 7.4 | — |
| Compound of Example 16 | 7.0 | — | — |
| Compound of Example 17 | — | 28 | 38 |
| Compound of Example 18 | — | 27 | — |
| Compound of Example 19 | — | 42 | — |
| Compound of Example 20 | — | 58 | — |
| Compound of Example 21 | 45 | — | — |
| Compound of Example 22 | — | 5 | — |
| Compound of Example 23 | — | 19 | — |
| Compound of Example 24 | — | 21 | — |
| Compound of Example 25 | — | 43 | — |
| Compound of Example 26 | — | 58 | — |
| Compound of Example 27 | — | 47 | — |
| Compound of Example 28 | — | 47 | — |
| Compound of Example 29 | — | 38 | — |
| Compound of Example 30 | — | 65 | — |

As clearly shown in Table 9, the 3,4-dihydroxychalcone derivatives showed clear inhibition activity against arachidonic acid-induced ear swelling. It is therefore seen that these 3,4-dihydroxychalcone derivatives have topical anti-inflammatory activity.

CELL PROTECTING ACTIVITY TEST

The 3,4-dihydroxychalcone derivatives obtained in Examples 1 to 30, as test compounds, were subjected to the following inhibition test against the lipid peroxidation reaction of liver microsome, which is an injured cell model. And, on the basis of the test results, the activities of the 3,4-dihydroxychalcone derivatives against the oxidation of cytoplasmic membranes were examined.

Rat liver microsome was prepared by a conventional method, and then suspended in 1.15% KCl to obtain a microsome suspension.

Then, the above microsome suspension in an amount of 2 mg as a protein was added to a tris-HCl buffer (pH 7.4) containing NADPH (final concentration 0.2 mM), ADP (final concentration 1 mM) and FeCl₃ (final concentration 10 μM). And, 10 μl of a dimethylformamide (DMF) solution of one of the test compounds was added such that the total amount was 1 ml, and the mixture was heated at 37° C. for 20 minutes. In this case, each test compound was added in such an amount that their final concentration was $10^{-5}$M each.

Thereafter, the formed lipid peroxide was measured for its amount by a thiobarbituric acid method. The activity of each test compound was expressed as an inhibition ratio (%) in comparison with that of a control group. For the control group, 10 μl of the DMF solution of the test compound was replaced with 10 μl of a DMF solution.

As a result, all the 3,4-dihydroxychalcone derivatives inhibited the lipid peroxidation reaction by 60% or more when used in a concentration of $10^{-5}$M. These results show that these 3,4-dihydroxychalcone derivatives have excellent inhibition activity against the oxidation of cytoplasmic membranes.

CYCLOOXYGENASE INHIBITING ACTIVITY TEST

A 50 mM phosphoric acid buffer solution (pH 7.4) containing sheep seminal vesicle, 2 mM of glutathione, 0.6 mM of epinephrine and 80 μM of EDTA-2Na preheated at 37° C. for 2 minutes, and then $^{14}$C-arachidonic acid was added to the reaction mixture. The mixture was heated for 10 minutes to form prostaglandin $E_2$, and the radiation activity of the formed prostaglandin $E_2$ was taken as cyclooxygenase activity.

The 3,4-dihydroxychalcone derivatives shown in Table 10 were selected as test compounds. The cyclooxygenase inhibiting activity of each test compound was evaluated as follows. Each test compound was independently added to the above phosphoric acid buffer solution, and the radiation activity of the formed prostaglandin $E_2$ was measured in the same manner as above. The inhibition ratio of each test compound was determined in comparison with that of the control group, and the value of $IC_{50}$ was calculated by a conventional method.

Table 10 shows $IC_{50}$ of each test compound.

TABLE 10

|  | Cyclooxygenase inhibiting activity ($IC_{50}$:μM) |
|---|---|
| Compound of Example 1 | 17.1 |
| Compound of Example 2 | 156.4 |
| Compound of Example 3 | 169.4 |
| Compound of Example 4 | 64.8 |
| Compound of Example 5 | 121.4 |
| Compound of Example 6 | 41.3 |
| Compound of Example 7 | 37.3 |
| Compound of Example 10 | 128.9 |
| Compound of Example 11 | 29.7 |
| Compound of Example 13 | 26.0 |
| Compound of Example 14 | 59.9 |
| Compound of Example 15 | 3.2 |
| Compound of Example 16 | 24.4 |
| Compound of Example 17 | 71.0 |
| Compound of Example 18 | 210.2 |
| Compound of Example 19 | 35.3 |
| Compound of Example 20 | 15.1 |
| Compound of Example 21 | 487.7 |
| Compound of Example 23 | 40.6 |
| Compound of Example 24 | 807.6 |
| Compound of Example 25 | 40.5 |
| Compound of Example 26 | 43.7 |
| Compound of Example 27 | 275.0 |
| Compound of Example 29 | 828.6 |

As clearly shown in Table 10, the $IC_{50}$ values of the above 3,4-dihydroxychalcone derivatives are small, and it is therefore seen that these 3,4-dihydroxychalcone derivatives have excellent cyclooxygenase inhibiting activity.

5-LIPOXYGENASE INHIBITING ACTIVITY TEST

RBL-1 cell homogenate was suspended in a 50 mM phosphoric acid buffer solution (pH 7.4) containing 2 mM of $CaCl_2$, 0.25 mM of sucrose, 1 mM of EDTA-2Na and glutathione, and the mixture was heated to 37° C. Arachidonic acid was added to the mixture to form 5-HETE (5-hydroxyeicosatetraenoic acid), and the 5-HETE was measured for an amount by a high-performance liquid chromatography.

The 3,4-dihydroxychalcone derivatives shown in Table 11 were selected as test compounds. The 5-lipoxygenase inhibiting activity of each test compound was evaluated as follows. Each test compound was independently added to the above phosphoric acid buffer solution, and the 5-HETE amount was measured in the same manner as above. The inhibition ratio of each test compound was determined in comparison with that of the control group, and the value of $IC_{50}$ was calculated by a conventional method.

Table 10 shows $IC_{50}$ of each test compound.

TABLE 11

|  | 5-Lipoxygenase inhibiting activity ($IC_{50}$:μM) |
|---|---|
| Compound of Example 1 | 0.0078 |
| Compound of Example 2 | 0.010 |
| Compound of Example 3 | 0.064 |
| Compound of Example 18 | 0.076 |
| Compound of Example 19 | 0.027 |
| Compound of Example 29 | 0.018 |
| Compound of Example 30 | 0.016 |

As clearly shown in Table 11, the $IC_{50}$ values of the above 3,4-dihydroxychalcone derivatives are small, and it is therefore seen that these 3,4-dihydroxychalcone derivatives have excellent lipoxygenase inhibiting activity.

PREPARATION EXAMPLE 1

Preparation of Ointment

A hydrophilic ointment of the Japanese Pharmacopoeia was selected as a matrix. A small amount taken from the matrix and 1 g of 2', 5'-dimethoxy-3,4-dihydroxychalcone were fully kneaded, and the remaining matrix was added. The mixture was fully kneaded and homogenized to give 100 g of an ointment.

Further, ointments were also prepared from the same 3,4-dihydroxychalcone derivatives as those obtained in Examples 2, 8, 10, 15 and 30 in the same manner as above.

PREPARATION EXAMPLE 2

Preparation of Ointment 100 grams of an ointment was prepared in the same manner as in Example 1 except that the matrix was replaced with an absorption ointment of the Japanese Pharmacopoeia.

Further, ointments were also prepared from the same 3,4-dihydroxychalcone derivatives as those obtained in Examples 2, 8, 10, 15 and 30 in the same manner as above.

PREPARATION EXAMPLE 3

Preparation of Tablet

| 3,4-Dihydroxychalcone derivative obtained in Example 1 | 50 g |
|---|---|
| Lactose | 10 g |
| Corn starch | 30 g |
| Crystalline cellulose | 8 g |
| Hydroxypropyl cellulose | 1 g |

-continued

| Magnesium stearate | 1 g |

Procedures

The 3,4-dihydroxychalcone derivative obtained in Example 1, lactose, corn starch and crystalline cellulose were taken in the above amounts, and mixed. A solution of hydroxypropyl cellulose (1 g) in 30 ml of water was added to the mixture, and the mixture was fully kneaded. The resultant kneaded mixture was granulated in a granular form by putting it through a 20-mesh sieve, and dried. Magnesium stearate (1 g) was mixed with the resultant granules, and the mixture was formed into tablets having a weight of 100 mg each.

Tablets were also prepared from the same 3,4-dihydroxychalcone derivatives as those obtained in Examples 2, 8, 10, 15 and 30 in the same manner as above.

PREPARATION EXAMPLE 4

Preparation of Injection Solution

| | |
|---|---|
| 3,4-Dihydroxychalcone derivative obtained in Example 1 | 10 mg |
| Sodium chloride | 90 mg |
| Distilled water for injection, containing 5% Na$_2$CO$_3$ | proper amount |
| Distilled water for injection | proper amount |
| | 10 ml |

PROCEDURES

The 3,4-dihydroxychalcone derivative obtained in Example 1 in the above-prescribed amount was dissolved in distilled water for injection containing 5% Na$_2$CO$_3$, and further, sodium chloride in the above-prescribed amount was also dissolved. Then, distilled water for injection was added until the total amount of the mixed solution was 10 ml. The so-obtained mixed solution was charged into an ampoule, and the ampoule was flushed with a nitrogen gas and flame-sealed to give an injection solution.

Injection solutions were also prepared from the same 3,4-dihydroxychalcone derivatives as those obtained in Examples 2, 8, 10, 15 and 30 in the same manner as above.

As explained above, the novel 3,4-dihydroxychalcone derivatives and the pharmaceutical preparations containing one of the 3,4-dihydroxychalcone derivatives as an active ingredient, provided by the present invention, have at least one of the anti-inflammatory activity, inhibiting activity against the oxidation of mammalian cytoplasmic membrane, cyclooxygenase inhibiting activity and lipoxygenase inhibiting activity.

When the present invention is worked, therefore, there can be provided novel anti-inflammatory preparations.

What is claimed is:

1. 3,4-Dihydroxychalcone derivatives which are compounds of the formula [I],

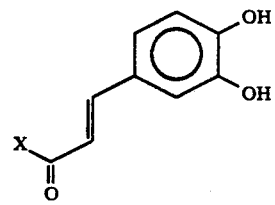

wherein X is a substituted phenyl group represented by the formula (i),

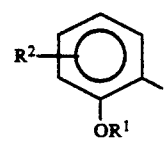

in which $R^1$ is a hydrogen atom or an alkyl group and $R^2$ is an alkyl group, an alkoxy group or an —OH group (excluding an OH-group in the 4-position), the formula (ii),

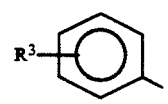

in which $R^3$ is an alkyl group, an alkoxy group or a dimethylamino group, the formula (iii),

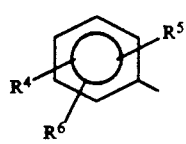

in which each of $R^4$ and $R^5$ is an alkyl group and $R^6$ is a hydrogen atom or an alkyl group, or the formula (iv),

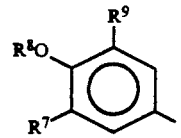

in which $R^7$ is an alkoxy group, $R^8$ is a hydrogen atom or an alkyl group and $R^9$ is a hydrogen atom or an alkoxy group, or salts thereof.

2. 3,4-Dihydroxychalcone derivatives according to claim 1, wherein each of the alkyl group as $R^1$ and the alkyl group as $R^2$ is independently methyl, ethyl, n-propyl, isopropyl, n-butyl, isobutyl or tert-butyl.

3. 3,4-Dihydroxychalcone derivatives according to claim 1, wherein the alkoxy group as $R^3$ is methoxy, ethoxy, n-propoxy, isopropoxy, n-butoxy, isobutoxy or tert-butoxy.

4. 3,4-Dihydroxychalcone derivatives according to claim 1, wherein the alkyl group as $R^3$ is methyl, ethyl, n-propyl, isopropyl, n-butyl, isobutyl or tert-butyl.

5. 3,4-Dihydroxychalcone derivatives according to claim 1, wherein the alkoxy group as $R^3$ is methoxy, ethoxy, n-propoxy, isopropoxy, n-butoxy, isobutoxy or tert-butoxy.

6. 3,4-Dihydroxychalcone derivatives according to claim 1, wherein each of the alkyl group as $R^4$, the alkyl group as $R^5$ and the alkyl group as $R^6$ is independently methyl, ethyl, n-propyl, isopropyl, n-butyl, isobutyl or tert-butyl.

7. 3,4-Dihydroxychalcone derivatives according to claim 1, wherein each of the alkoxy group as $R^7$ and the alkoxy group as $R^9$ is independently methoxy, ethoxy, n-propoxy, isopropoxy, n-butoxy, isobutoxy or tert-butoxy.

8. 3,4-Dihydroxychalcone derivatives according to claim 1, wherein the alkyl group as $R^8$ is methyl, ethyl, n-propyl, isopropyl, n-butyl, isobutyl or tert-butyl.

9. An anti-inflammatory preparation containing, as an active ingredient, one of the 3,4-dihydroxychalcone derivatives recited in claim 1.

10. An anti-inflammatory preparation according to claim 9, wherein at least one other additive selected from a vehicle, a binder, a lubricant, a disintegrant, an antiseptic, an isotonicity-forming agent, a stabilizer, a dispersion, an antioxidant, a colorant, a flavor and a buffer is contained.

11. An anti-inflammatory preparation according to claim 9, wherein one of the 3,4-Dihydroxychalcone derivatives of the formula (I) is contained in an amount of 0.01 to 99% by weight.

* * * * *